US008139577B2

(12) United States Patent  
Wang et al.

(10) Patent No.: US 8,139,577 B2  
(45) Date of Patent: Mar. 20, 2012

(54) DATA COLLECTING METHOD AND A MASTER DEVICE AND A SLAVE DEVICE THEREFOR

(75) Inventors: Yuh-Ching Wang, Tainan (TW); Yu-Hsien Chiu, Kaohsiung County (TW)

(73) Assignee: Industrial Technology Research Institute, Hsinchu (TW)

( * ) Notice: Subject to any disclaimer, the term of this patent is extended or adjusted under 35 U.S.C. 154(b) by 193 days.

(21) Appl. No.: 12/428,658

(22) Filed: Apr. 23, 2009

(65) Prior Publication Data

US 2010/0189102 A1 Jul. 29, 2010

(30) Foreign Application Priority Data

Jan. 23, 2009 (TW) .............................. 98102966 A

(51) Int. Cl.
*H04L 12/28* (2006.01)
*H04L 12/56* (2006.01)
*G06F 15/16* (2006.01)

(52) U.S. Cl. ........ 370/389; 709/208; 709/209; 709/210; 709/211

(58) Field of Classification Search .................. 370/389; 709/208, 209, 210, 211
See application file for complete search history.

(56) References Cited

U.S. PATENT DOCUMENTS

| 5,890,054 | A | * | 3/1999 | Logsdon et al. | ............. 455/11.1 |
| 6,518,889 | B2 | | 2/2003 | Schlager et al. | |
| 2002/0136162 | A1 | * | 9/2002 | Yoshimura et al. | ........... 370/229 |
| 2003/0135622 | A1 | * | 7/2003 | Anderson et al. | ............. 709/227 |
| 2006/0031378 | A1 | * | 2/2006 | Vallapureddy et al. | ........ 709/208 |
| 2006/0168730 | A1 | * | 8/2006 | Menkedick et al. | ............. 5/618 |
| 2007/0072547 | A1 | * | 3/2007 | Sims et al. | ........................ 455/39 |
| 2008/0167566 | A1 | * | 7/2008 | Unver et al. | .................. 600/513 |
| 2009/0097623 | A1 | * | 4/2009 | Bharadwaj | ............... 379/106.02 |

FOREIGN PATENT DOCUMENTS

| TW | 357078 | 5/1999 |
| TW | 483747 | 4/2002 |
| TW | 495355 | 7/2002 |
| TW | 558440 | 10/2003 |
| TW | 588840 | 5/2004 |
| TW | M268002 | 6/2005 |
| TW | M288176 | 3/2006 |
| TW | I292707 | 6/2006 |
| TW | 294589 | 7/2006 |
| TW | I245614 | 7/2006 |
| TW | I294000 | 7/2006 |

(Continued)

OTHER PUBLICATIONS

CAN in Automation (CiA): CAN protocol. CAN in Automation (CiA): Controller Area Network (CAN). CAN in Automation (CiA), n.d. Web. Dec. 13, 2011. <http://www.can-cia.de/index.php?id=systemdesign-can-protocol>.*

(Continued)

*Primary Examiner* — Ayaz Sheikh  
*Assistant Examiner* — Tarell Hampton  
(74) *Attorney, Agent, or Firm* — ThomasIKayden

(57) ABSTRACT

A data collecting method and a master device and a slave device therefor are provided. The method includes the following steps. The slave device receives an environment voice and accordingly generates an audio data. The slave device outputs the audio data through packets of a predetermined format according to a control area network protocol. The master device receives the audio data.

15 Claims, 5 Drawing Sheets

FOREIGN PATENT DOCUMENTS

| | | |
|---|---|---|
| TW | I294280 | 7/2006 |
| TW | I260979 | 9/2006 |
| TW | 200701973 | 1/2007 |
| TW | I274576 | 3/2007 |
| TW | M308759 | 4/2007 |
| TW | M309299 | 4/2007 |
| TW | 200726440 | 7/2007 |
| TW | 200730134 | 8/2007 |
| TW | 200737056 | 10/2007 |
| TW | 200806256 | 2/2008 |
| TW | M327717 | 3/2008 |
| TW | 200820754 | 5/2008 |

OTHER PUBLICATIONS

English Abstract of TW200737056.
English Abstract of TW357078.
English Abstract of TW200806256.
English Abstract of TW588840.
English Abstract of TW I245614.
English Abstract of TW200820754.
English Abstract of TW I260979.
English Abstract of TW200701973.
English Abstract of TW558440.
English Abstract of TW M309299.
English Abstract of TW M268002.
English Abstract of TW M327717.
English Abstract of TW M288176.
English Abstract of TW200730134.
English Abstract of TW483747.

* cited by examiner

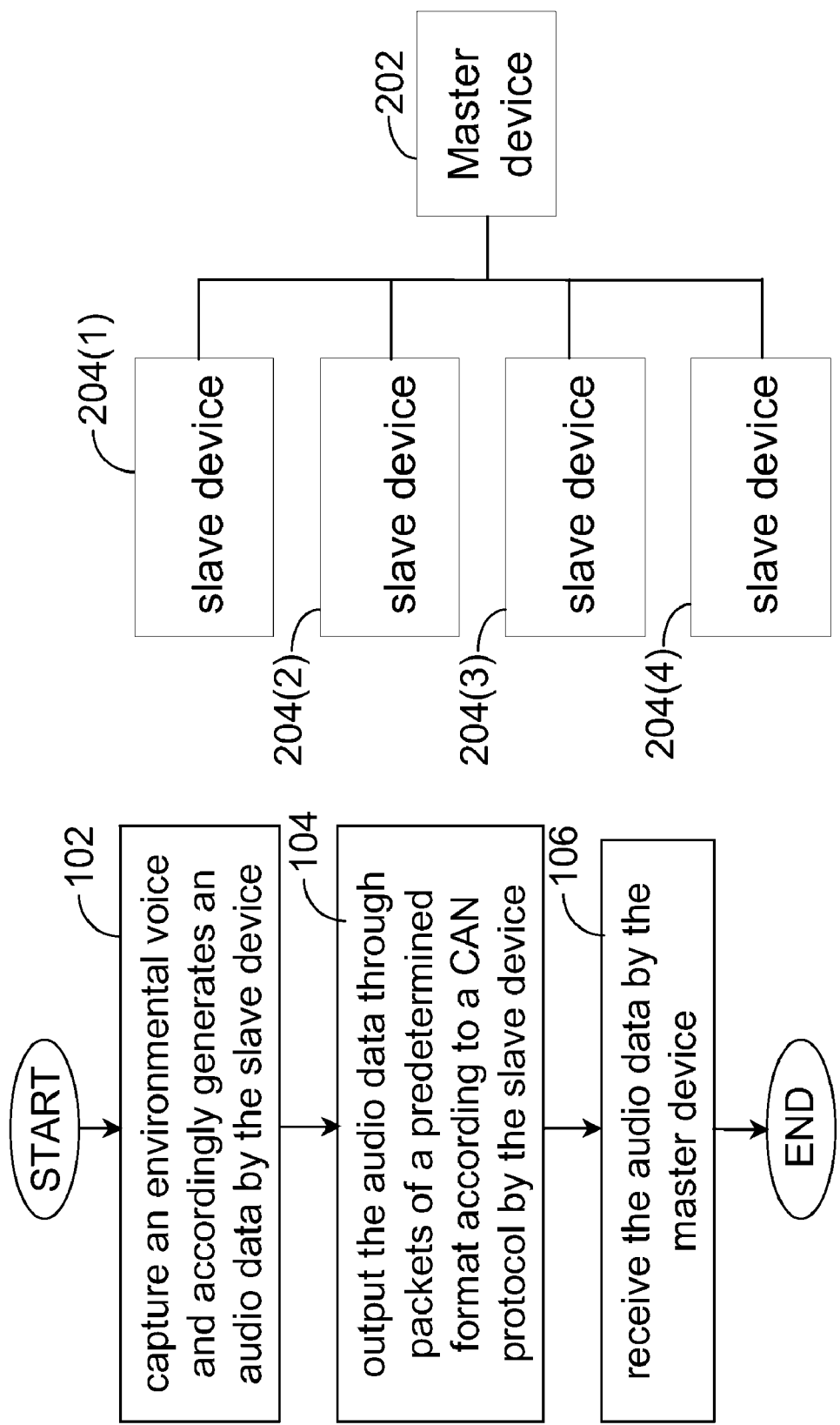

| emergency identification | slave device identification | event identification |
|---|---|---|

FIG. 4A

| master device request identification | slave device mapping identification | service identification |
|---|---|---|

FIG. 4B

| slave device response identification | slave device identification | service identification response identification |
|---|---|---|

FIG. 4C

| audio data identification | slave device identification | sequence number |
|---|---|---|

FIG. 4D

| 10 | 9 | 8 | 7 | 6 | 5 | 4 | 3 | 2 | 1 | 0 | |
|---|---|---|---|---|---|---|---|---|---|---|---|
| | | | | | | | | | | | identification bit |
| 0 | 0 | slave device identification | | event identification | | | | reserved | | | emergency event message |
| 0 | 1 | slave device mapping identification | | | service identification | | | reserved | | | request message |
| 1 | 0 | slave device identification | | service identification | | | response identification | | reserved | | response message |
| 1 | 1 | slave device identification | | sequence number | | | | | | | audio data |

FIG. 5

DATA COLLECTING METHOD AND A MASTER DEVICE AND A SLAVE DEVICE THEREFOR

This application claims the benefit of Taiwan application Serial No. 98102966, filed Jan. 23, 2009, the subject matter of which is incorporated herein by reference.

BACKGROUND

1. Field

The invention relates in general to a data collecting method and a master device and a slave device therefor.

2. Description of the Related Art

Along with the coming of the ageing society, the financial expenditure on the healthcare system has become a heavy burden to more and more countries. Thus, how to reduce the cost of healthcare has become a focus of policies to the governments of many countries. In recent years, the telecommunication technology has often been used in related home-care services to reduce the cost of healthcare.

Nowadays, the problem of the elderly people living alone has attracted more and more attention in many countries. Elderly people living alone without family members or healthcare givers to look after them may miss the opportunity of first aid when they are attacked by an unexpected onset of illness. Thus, a healthcare system with actively notifying function or risk warning function is a direction in the research and development of healthcare system.

The current method of collecting and transmitting data via the Internet can transmit data by way of multiplexing transmission. However, the Internet cannot assure the arrival time of the packet of data, so the current method cannot assure the synchronicity of multiple items of audio data.

SUMMARY

The exemplary embodiments of the invention relates to a data collecting method and a master device and a slave device therefor which are suitable to be used in a healthcare system. The invention integrates and synchronizes multiple signals, so that the healthcare system can promptly and correctly determines the state of a healthcare receiver.

According to the exemplary embodiments of the invention, a data collecting method is provided. The method includes the following steps. The slave device receives an environment voice and accordingly generates an audio data. The slave device outputs the audio data through packets of a predetermined format according to a control area network protocol. The master device receives the audio data.

According to the exemplary embodiments of the invention, a slave device is provided. The slave device includes a controlling unit, an audio capturing unit and a transceiver. The audio capturing unit, under the control of the controlling unit, is for capturing an environmental voice and generating an audio data corresponding to the environmental voice. The transceiver is for outputting the audio data through packets of a predetermined format according to a CAN protocol.

According to the exemplary embodiments of the invention, a master device is provided. The master device includes a transceiver and a processing unit. The transceiver is for receiving an audio data transmitted through packets of a predetermined format according to a CAN protocol. The processing unit processes the audio data. The audio data is correspondingly generated from an environmental voice captured by a slave device.

The invention will become apparent from the following detailed description of the preferred but non-limiting embodiments. The following description is made with reference to the accompanying drawings.

BRIEF DESCRIPTION OF THE DRAWINGS

FIG. 1 shows a flowchart of a data collecting method of an embodiment of the invention;

FIG. 2 shows a block diagram of a data collecting system used in the data collecting method of FIG. 1;

FIGS. 4A~4D show an example of the contents of the header of the above packet of a predetermined format;

FIG. 5 shows an example of the header of the packet of the predetermined format.

DESCRIPTION OF THE EMBODIMENTS

The invention provides a data collecting method and a master device and a slave device therefor. Referring to both FIG. 1 and FIG. 2. FIG. 1 shows a flowchart of a data collecting method of an embodiment of the invention. FIG. 2 shows a block diagram of a data collecting system used in the data collecting method of FIG. 1. The data collecting system 200 includes a master device 202 and at least one slave device 204. The master device 202 receives the data from at least one slave device 204. For example, the data collecting system 200 has four slave devices 204 (1)~204 (4). In the present embodiment of the invention, the slave device 204 (4) is used for exemplification, and the slave device 204 denotes one of the slave devices 204 (1)~204 (4).

In step 102 of FIG. 1, the slave device 204 (4) captures an environmental voice and accordingly generates an audio data VS. In step 104, the slave device 204 (4) outputs the audio data VS through packets of a predetermined format according to a control area network (CAN) protocol. In step 106, the master device 202 receives the audio data VS.

Figure 3B:
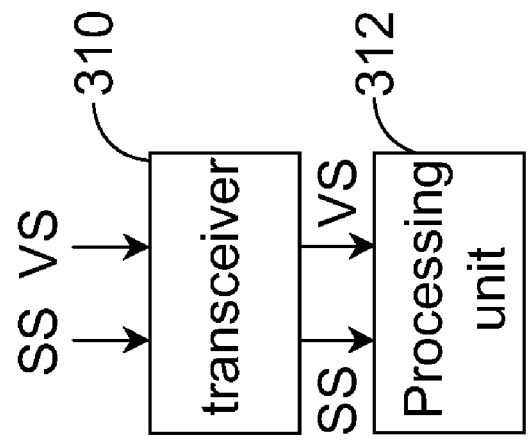
FIG. 3B shows an example of a block diagram of a master device of FIG. 2.
Figure 3A:
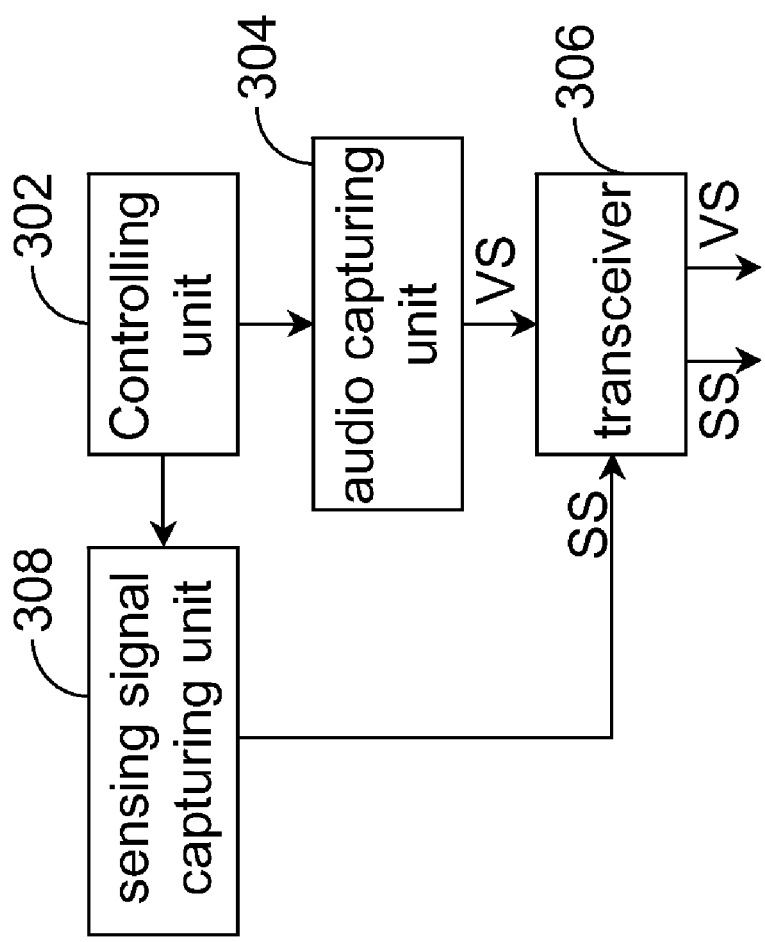
FIG. 3A shows an example of a block diagram of a slave device of FIG. 2.

FIG. 3A shows an example of a block diagram of a slave device 204 (4) of FIG. 2. FIG. 3B shows an example of a block diagram of a master device 202 of FIG. 2. The slave device 204 (4) includes a controlling unit 302, an audio capturing unit 304, and a transceiver 306. The audio capturing unit 304, under the control of the controlling unit 302, captures an environmental voice and generates an audio data VS corresponding to the environmental voice. The transceiver 306 outputs the audio data VS through packets of a predetermined format according to the CAN protocol.

The master device 202 includes a transceiver 310 and a processing unit 312. The transceiver 310 receives the audio data VS through a packet of the predetermined format according to the CAN protocol. The processing unit 312 processes the audio data VS.

Preferably, as indicated in FIG. 3A, the slave device 204 (4) further includes a sensing signal capturing unit 308. The sensing signal capturing unit 308, under the control of the controlling unit 302, senses an environmental attribute value to accordingly generate a sensing signal SS. The environmental attribute value is the value of one of the attributes such as pressure, temperature, switch ON/OFF state, humidity, and physiological state. The transceiver 306 further outputs the sensing signal SS by a packet of the predetermined format according to the CAN protocol.

Correspondingly, the transceiver 310 of the master device 202 receives the sensing signal SS transmitted through a packet of the predetermined format according to the CAN protocol. The processing unit 312 further processes the sensing signal SS.

It can be implemented that only some of the slave devices 204 (1)~204 (4) of FIG. 1 have the sensing signal capturing unit 308. For example, only the slave device 204 (4) has the sensing signal capturing unit 308. Whether the slave devices 204 (1)~204 (4) have the sensing signal capturing unit 308 or not individually is determined according to actual needs.

The slave devices 204 (1)~204 (4) can be disposed at different positions at the residence of the healthcare receiver according to actual needs. For example, the slave devices 204 (1)~204 (4) can respectively be disposed at the lounge, the bedroom, the stair room, and the rest room. Thus, the slave devices 204 (1)~204 (4) can capture various sounds generated from various activities of the healthcare receiver. Examples of the sounds include the sound generated when the healthcare receiver walks, gets on/off the bed or wheelchair, opens/closes the door, uses the faucet, passes water/soil, flushes the toilet, drinks water, falls over, gets choked, calls, cries for help, has an unexpected onset of illness, or damages things, or when things topple down.

The slave device 204 (4) equipped with the sensing signal capturing unit 308 can sense other environmental attribute values at the same time. When the slave device 204 (4) is disposed at the rest room, the sensing signal capturing unit 308 of the slave device 204 (4), for example, is a pressure sensor deposed on a toilet flush button or a switch sensor disposed on a faucet.

After having collected all of the audio data VS and the sensing signal SS outputted from the slave devices 204 (1)~204 (4), the master device 202 can integrate at least a part of the signals being received to determine the events occurring to the healthcare receiver. The master device 202 can also transmit the integrated information to the healthcare center located at a remote end to inform the healthcare giver in the healthcare center of the current state of the healthcare receiver so that the healthcare giver can take suitable actions.

Compared with the packet of the Internet, the packet according to the CAN protocol further has the feature of instant transmission. Both the audio data VS and the sensing signal SS are transmitted through packets according to the CAN protocol. As both the audio data VS and the sensing signal SS outputted from the slave device 204 (1)~204 (4) can be transmitted to the master device 202 almost instantly, it is fair to say that the audio data VS and the sensing signal SS outputted from the slave device 204 (1)~204 (4) are almost transmitted to the master device 202 at the same time. Thus, the master device 202 can easily integrate the audio data VS and the sensing signal SS outputted from the slave devices 204 (1)~204 (4) to further increase the accuracy in the determination of subsequent events.

For example, suppose that the slave devices 204 (3) and 204 (4) are respectively disposed on the wall and on the toilet flush button of a rest room. If the slave device 204 (3) outputs an audio data VS corresponding to the sound of flushing the toilet and the slave device 204 (4) outputs a sensing signal SS generated when the toilet flush button is pressed, then the master device 202 almost receives the audio data VS and the sensing signal SS at the same time. Thus, the master device 202 can determine that there is an event of "using toilet". Or, the master device 202 integrates the audio data VS and the sensing signal SS, and then transmits the integrated result to the healthcare center, so that the healthcare center can also determine that there is an event of "using toilet" according to the audio data VS and the sensing signal SS which are almost received at the same time.

The master device 202 can also synchronize or integrate the audio data VS outputted from two different the slave devices 204 so that the result can be used in the determination of events.

When some environmental voices or environmental attribute values occur, the slave device 204 can determine that there is an emergency event and actively sends an emergency message to the master device 202.

The way of converting an environmental voice into an audio data VS by the audio capturing unit 304 of the slave device 204 is exemplified below. Firstly, the audio capturing unit 304 samples and quantifies the analog signals of the environmental voices being captured by an analog-to-digital converter (ADC) to generate multiple consecutive sampling values. Next, let a unit be 8 bits, and a suitable amount of sampling values is written into the payload of a CAN packet as the above audio data VS. In an example, the sampling frequency of the slave device 204 is 8000 Hz; each sampling value is denoted by 8 bits, and 1000 serial packets of the audio data VS are transmitted in a second. In the present embodiment of the invention, the size of available sampling frequency and the size of the data volume of the audio data VS contained in each packet are calculated according to the bandwidth of the CAN protocol, so that the audio data VS being transmitted can achieve the effect of instant transmission.

Referring to FIGS. 4A~4D, an example of the contents of the header of the above packets of the predetermined format is shown. In the present embodiment of the invention, the format of the packet of the predetermined format is defined by the header of the CAN packet. The header of the packet of the predetermined format has a message identification field for recording an emergency identification, a master device request identification, a slave device response identification, and an audio data identification.

When the slave device 204 transmits an emergency message to the master device 202 through a packet of the predetermined format, as indicated in FIG. 4A, meanwhile, the message identification field of the header of the packet of the emergency event message records an emergency identification. The header of the packet further has a slave device identification and an event identification. The slave device identification is, for example, the identification ID of the media access control (MAC) of the slave device 204. Different emergency events correspond to different event identifications.

The master device 202 can further transmits a request message to the slave device 204 through a packet of the predetermined format. As indicated in FIG. 4B, the message identification field of the header of the packet of the request message records the master device request identification. The header of the packet further has a slave device mapping code and a service identification. The slave device mapping code is for determining at least one of multiple corresponding slave devices 204. The service identification is for determining a corresponding action.

For example, each bit of the slave device mapping code is respectively mapped and corresponds to one slave device 204, so that the master device 202 can request one or multiple slave devices 204 at the same time. The service identification is the service requested by the master device. Examples of the services include obtaining the attribute GetAttribute, setting the attribute SetAttribute, activating the transmission StartAudio of the audio data, and terminating the transmission StopAudio of the audio data.

When the slave device 204 receives a request message from the master device 202, the slave device 204 immediately executes a corresponding action and sends a response message to the master device. As indicated in FIG. 4C, the message identification field of the header of the packet of the response message records the response identification of the slave device. The header of the packet further has a slave device identification, a service identification, and a response identification. The response identification is for recording the response such as success, error, or not otherwise provided (NOP).

The above sensing signal SS can be defined as a signal corresponding to a particular attribute, and the master device 202 can ask for obtaining the sensing signal SS by way of obtaining the service identification of the attribute GetAttribute. The sensing signal SS can be carried through the payload of the CAN packet of the response message transmitted from the slave device 204.

When the slave device 204 outputs the audio data VS through a packet of the predetermined format, as indicated in FIG. 4D, the message identification field of the header of the packet of the audio data VS records the audio data identification. The header of the packet further has a slave device identification and a sequence number for recording the sequence of the packet for transmitting the audio data VS. The sequence number can be re-cyclically. The packet whose sequence number is 0 can be used to transmit the time stamp, which is used in calibrating the synchronicity of the audio data VS.

Referring to FIG. 5, an example of the header of the packet of the predetermined format is shown. The format of the packet of the predetermined format is, for example, defined by the header of the CAN packet. That is, the format is defined by 11 identifier bits of the CAN packet. The first 2 bits are used as the message identification field. The emergency identification, the master device request identification, the slave device response identification, and the audio data identification are denoted by binary digits 00, 01, 10, and 11, respectively. What are transmitted by other identifier bits are indicated in FIG. 5.

Figure 6:
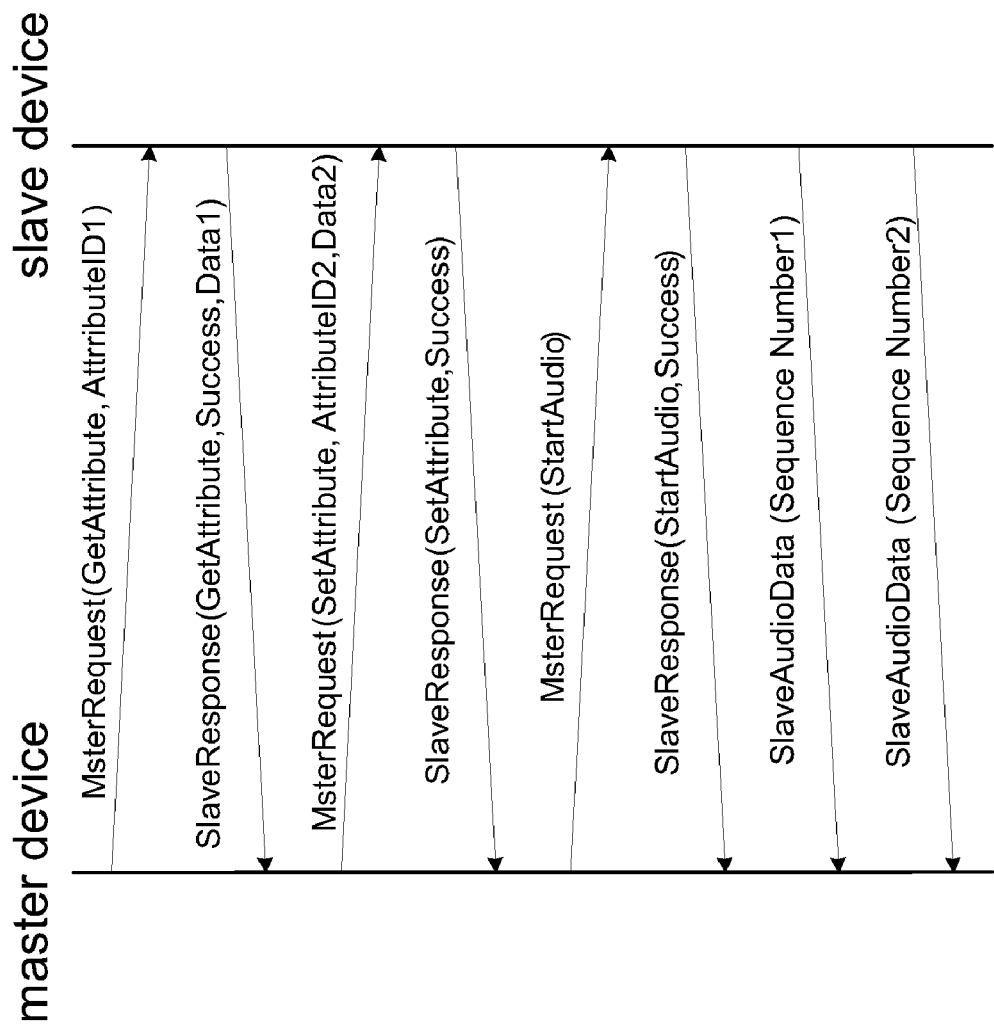
FIG. 6 shows an example of message communication between the master device and the slave device of FIG. 2.

Referring to FIG. 6, an example of message communication between the master device 202 and the slave device 204 of FIG. 2 is shown. The master device 202 first of all sends a request message MasterRequest (GetAttribute, AttributeID1) to the slave device 204 to ask for obtaining the attribute corresponding to the attribute identification AttributeID1. Then, the slave device 204 responds such request by sending a response message SlaveResponse (GetAttribute, Success, Data1) to the master device 202. The packet of the response message includes a response identification denoting Success and an attribute Data1 denoting attribute identification AttributeID1. Then, the master device 202 sends a request message MasterRequest (SetAttribute, AttributeID2, Data2) to the slave device 204 to ask for setting the attribute of the slave device 204 corresponding to the attribute identification AttributeID2 as Data2.

Then, after the setting of the slave device 204 is done, the slave device 204 responds to one response message SlaveResponse (SetAttribute, Success) including a success identification Success. After that, the master device 202 sends a request message MasterRequest (StartAudio) to the slave device 204 to ask for activating the transmission of the audio data. The slave device 204 responds to one response message SlaveResponse (StartAudio, Success) including a success identification Success, and starts to transmit the packets of SlaveAudioData (SequeceNumber1) and SlaveAudioData (SequeceNumber2), wherein the audio data of the packets have the sequence numbers SequeceNumber1 and SequeceNumber2.

In the present embodiment of the invention, the environmental voice is selectively captured and provided to the healthcare system as a basis of determining events. When integrating multiple items of audio data outputted from different slave devices or integrating the audio data with the sensing signal outputted from other slave devices as a basis of determining events, the present embodiment of the invention enables multiple items of to-be-integrated data or signals to achieve excellent synchronicity so that the accuracy in determining events is increased.

According to the method of transmitting the audio data via an analog line, despite the audio data can be stably transmitted via the analog line, each line can only transmit the audio data of one slave device only and cannot transmit the data or signals outputted from other slave devices. Compared with the method of transmitting the audio data via an analog line, the invention can transmit the audio data outputted from multiple slave devices or even can transmit various types of data or signals.

According to the data collecting method and the master device and the slave device therefor disclosed in the invention, the master device can synchronically collect the audio data outputted from multiple slave devices or even synchronically collect the audio data and the sensing signals outputted from multiple slave devices. Thus, the integration between various data is made easier, and the data collected according to the invention can have wider range of application. Moreover, the invention enables the healthcare system using the same to promptly and correctly determine the state of the healthcare receiver and the event occurring to the healthcare receiver, and is thus competitive in the market.

While the invention has been described by way of example and in terms of a preferred embodiment, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:
1. A data collecting method, comprising:
capturing an environmental voice and accordingly generating an audio data by a slave device, wherein the environmental voice includes sound generated from activities of a healthcare receiver;
outputting the audio data through packets of a predetermined format according to a control area network (CAN) protocol by the slave device;
receiving the audio data by a master device, wherein the master device integrates information including the received audio data to determine an event occurring to the healthcare receiver;
transmitting a request message through at least one packet of the predetermined format to the slave device by the master device,
wherein the predetermined format for a packet is defined according to the CAN protocol, the header of the packet of the predetermined format has a message identification field for recording one of an emergency identification, a master device request identification, a slave device response identification, and an audio data identification;

wherein the at least one packet of the request message has the message identification field recording the master device request identification and has a slave device mapping code and a service identification, the slave device mapping code is for determining at least one of a plurality of slave devices corresponding to the request message, and the service identification is for determining a corresponding action.

2. The method according to claim 1, further comprising:
sensing an environmental attribute value and accordingly generating a sensing signal by the slave device;
outputting the sensing signal through the packets at least one packet of the predetermined format according to the CAN protocol by the slave device; and
receiving the sensing signal by the master device.

3. The method according to claim 2, wherein the environmental attribute value is the value of one of pressure, temperature, switch ON/OFF state, humidity, and physiological state.

4. The method according to claim 1, wherein in the packet for transmitting the audio data, the message identification field records the audio data identification, and the packet for transmitting the audio data further has a slave device identification and a sequence number.

5. A slave device, comprising:
a controlling unit;
an audio capturing unit, under the control of the controlling unit, for capturing an environmental voice and generating an audio data corresponding to the environmental voice, wherein the audio capturing unit captures the environmental voice including sound generated from activities including daily life of a healthcare receiver; and
a transceiver for outputting the audio data through packets of a predetermined format according to a control area network (CAN) protocol;
wherein the predetermined format for a packet is defined according to the CAN protocol, the header of the packet of the predetermined format has a message identification field for recording one of an emergency identification, a master device request identification, a slave device response identification, and an audio data identification;
wherein the packets for transmitting the audio data have the message identification field for recording an audio data identification and further have a slave device identification and a sequence number.

6. The slave device according to claim 5, further comprising:
a sensing signal capturing unit, under the control of the controlling unit, for sensing an environmental attribute value to accordingly generate a sensing signal;
wherein the transceiver is further for outputting the sensing signal through at least one packet of the predetermined format according to the CAN protocol.

7. The slave device according to claim 6, wherein the environmental attribute value is the value of one of pressure, temperature, switch ON/OFF state, humidity, and physiological state.

8. A master device, comprising:
a transceiver for receiving an audio data transmitted through packets of a predetermined format according to a control area network (CAN) protocol; and
a processing unit for processing the audio data and integrating information including the audio data to determine an event occurring to a healthcare receiver;
wherein the audio data is correspondingly generated from an environmental voice captured by a slave device, and the environmental voice includes sound generated from activities of the healthcare receiver;
wherein the predetermined format for a packet is defined according to the CAN protocol, the header of the packet of the predetermined format has a message identification field for recording one of an emergency identification, a master device request identification, a slave device response identification, and an audio data identification;
wherein the packets for transmitting the audio data have the message identification field for recording an audio data identification and further have a slave device identification and a sequence number.

9. The master device according to claim 8, wherein the transceiver is further for receiving a sensing signal transmitted through at least one packet of the predetermined format according to the CAN protocol, and the processing unit is further for processing the sensing signal;
wherein the sensing signal is correspondingly generated from an environmental attribute value captured by the slave device.

10. The master device according to claim 9, wherein the environmental attribute value is the value of one of pressure, temperature, switch ON/OFF state, humidity, and physiological state.

11. The master device according to claim 8, wherein the processing unit is further for generating a request message, and the transceiver is further for outputting the request message through at least one packet of the predetermined format according to the CAN protocol;
wherein in the at least one packet of request message, the message identification field records the master device request identification, the at least one packet of the request message further has a slave device mapping code and a service identification, the slave device mapping code is for determining at least one of a plurality of slave devices corresponding to the request message, and the service identification is for determining a corresponding action.

12. The master device according to claim 9, wherein the processing unit integrates the information including the audio data and the sensing signal to determine the event occurring to the healthcare receiver.

13. The method according to claim 2, wherein the master device integrates the information including the received audio data and the received sensing signal to determine the event occurring to the healthcare receiver.

14. A data collecting method, comprising:
capturing an environmental voice and accordingly generating an audio data by a slave device, wherein the environmental voice includes sound generated from activities of a healthcare receiver;
outputting the audio data through packets of a predetermined format according to a control area network (CAN) protocol by the slave device;
receiving the audio data by a master device, wherein the master device integrates information including the received audio data to determine an event occurring to the healthcare receiver;
wherein the predetermined format for a packet is defined according to the CAN protocol, the header of the packet of the predetermined format has a message identification field for recording one of an emergency identification, a master device request identification, a slave device response identification, and an audio data identification;
wherein in the packets for transmitting the audio data, the message identification field records the audio data identification, and the packet for transmitting the audio data further has a slave device identification and a sequence number.

15. A master device, comprising:
a transceiver for receiving an audio data transmitted through packets of a predetermined format according to a control area network (CAN) protocol; and
a processing unit for processing the audio data and integrating information including the audio data to determine an event occurring to a healthcare receiver;
wherein the audio data is correspondingly generated from an environmental voice captured by a slave device, and the environmental voice includes sound generated from activities of the healthcare receiver;
wherein the processing unit is further for generating a request message, and the transceiver is further for outputting the request message through at least one packet of the predetermined format according to the CAN protocol;
wherein the predetermined format for a packet is defined according to the CAN protocol, the header of the packet of the predetermined format has a message identification field for recording one of an emergency identification, a master device request identification, a slave device response identification, and an audio data identification;
wherein in the at least one packet of request message, the message identification field records the master device request identification, the at least one packet of the request message further has a slave device mapping code and a service identification, the slave device mapping code is for determining at least one of a plurality of slave devices corresponding to the request message, and the service identification is for determining a corresponding action.

* * * * *